United States Patent [19]

Muntwyler

[11] 4,080,329
[45] Mar. 21, 1978

[54] PROCESS FOR THE MANUFACTURE OF 2-MERCAPTO PYRIDINE-1-OXIDES

[75] Inventor: René Eric Muntwyler, Hofstetten, Switzerland

[73] Assignee: Ciba-Geigy Corporation, Ardsley, N.Y.

[21] Appl. No.: 673,241

[22] Filed: Apr. 2, 1976

[51] Int. Cl.$^2$ .......................................... C07D 213/89
[52] U.S. Cl. ...................... 260/294.8 G; 260/294.8 T; 260/295 AM; 260/296 R; 260/270 K
[58] Field of Search .................. 260/294.8 T, 294.8 G

[56] References Cited

U.S. PATENT DOCUMENTS 3,249,597   5/1966   Dehn et al. ......................... 260/156

OTHER PUBLICATIONS

Adams et al. J. Am. Chem. Soc. vol. 76 (10) May 20, 1954.
Abramovitch, Pyridine and its Derivatives, Supplement Part Two, Wiley Pub. pp. 221-225 (1974).
Klingsberg Pyridine and its Derivatives, Part Two Interscience Pub. (1961).
Ochiai, J. Org. Chem. vol. 18, pp. 534-542 (1953).
Fieser & Fieser, Advanced Organic Chemistry, Reinhold Pub. pp. 634-635 (1961).

*Primary Examiner*—Alan L. Rotman
*Attorney, Agent, or Firm*—Edward McC. Roberts; Prabodh I. Almaula

[57] ABSTRACT

A process for the manufacture of 2-mercaptopyridine-1-oxides and zinc salts thereof, comprising the steps of oxidizing a 2-acetylaminopyridine with peracetic acid in an inert solvent to give a 2-acetamidopyridine-1-oxide, cleaving the acetyl group with mineral acid to give a 2-aminopyridine-1-oxide, diazotizing the 2-aminopyridine-1-oxide and treating the diazonium salt with hydrochloric acid to give a 2-chloropyridine-1-oxide, treating the latter with a sulfhydryl-donor to give a 2-mercaptopyridine-1-oxide, and optionally treating the latter with a zinc salt to make the 2:1 zinc salt of the 2-mercaptopyridine-1-oxide. The resulting zinc salts are useful in anti-dandruff preparations.

5 Claims, No Drawings

PROCESS FOR THE MANUFACTURE OF 2-MERCAPTO PYRIDINE-1-OXIDES

BACKGROUND OF THE INVENTION

Heavy metal salts, particularly zinc salts of 2-mercaptopyridine-1-oxides have long been of interest as antibacterial agents. The zinc salt of 2-mercaptopyridine-N-oxide has found particular use in shampoos as an antidandruff agent.

Because of the utility of 2-mercaptopyridine-1-oxide and ring-substituted derivitives thereof, there has been a demand for a synthesis thereof which gives good yields of pure product, and which is generally applicable to the class of 2-mercaptopyridine-1-oxides. 2-Aminopyridine and ring-substituted derivitives thereof are generally cheap and readily available commercially. It is therefore an object of this invention to provide a process of manufacture for 2-mercaptopyridine-1-oxide and ring-substituted derivitives thereof, using 2-aminopyridine or ring-substituted derivitives thereof as the starting material. It is a further object of this invention to provide a process of manufacture, yielding the desired compounds, in high overall yield, with a minimum of purification. It is a further object of this invention to provide such a process of manufacture which requires little or no isolation of intermediates between the starting material and the final product.

The object of this invention has been realized by a process of manufacture, following the reaction scheme outlined below:

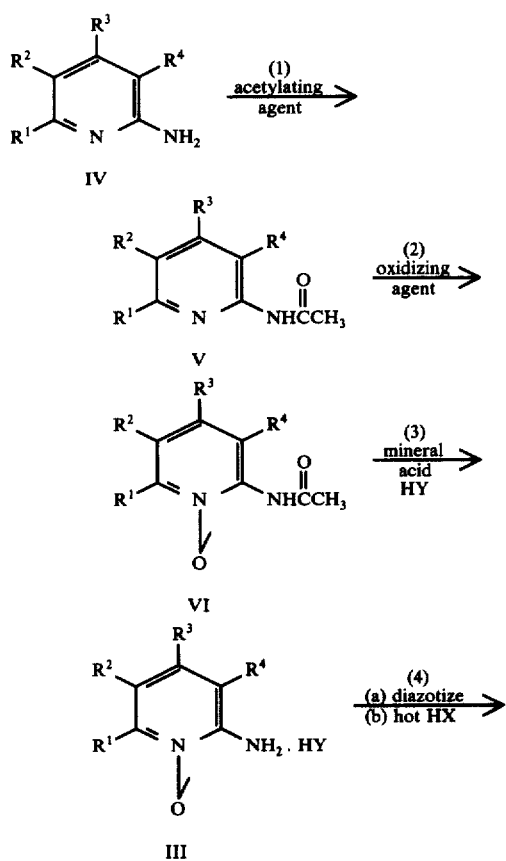

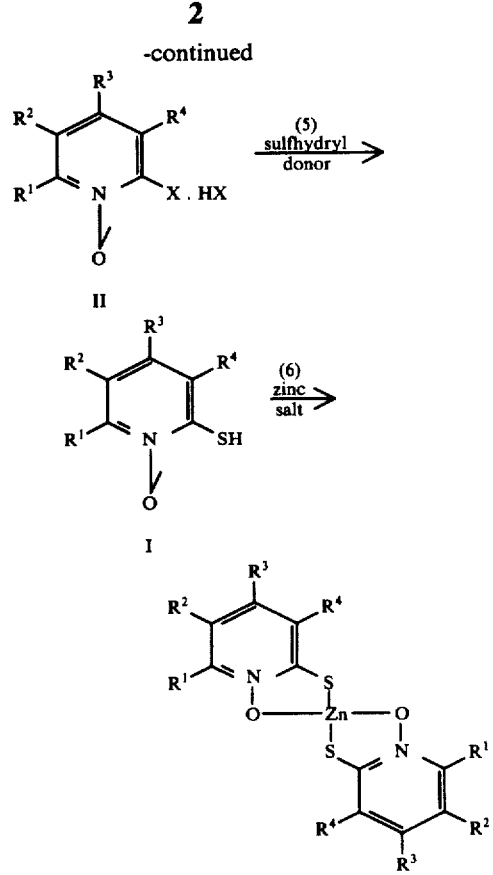

where X is Cl or Br,
Y is Cl, Br, $HSO_4$, or $BF_4$,
$R^1$, $R^2$, $R^3$ and $R^4$ are hydrogen, fluorine, chlorine, bromine, nitro, $C_1$ to $C_{12}$-alkyl, $C_1$ to $C_4$-alkoxy, benzyl, phenyl or phenoxy, provided at least two of $R^1$, $R^2$, $R^3$ and $R^4$ are hydrogen.

The process includes the steps of diazotizing a 2-aminopyridine-1-oxide salt in dilute hydrochloric acid, and treating the resulting diazonium salt with hydrochloric acid or hydrobromic acid to give the corresponding 2-chloro- or 2-bromo-pyridine-1-oxide as the corresponding hydrohalide salt, followed by treatment with a sulfhydryl donor to give the corresponding 2-mercaptopyridine-1-oxide.

The acetylating agent of step (1) is preferably acetic anhydride. Of course, other loweralkanoyl acylating agents can be used in place of acetylating agents, for instance, propionic anhydride, but acetylation is preferred as a matter of economics and ease.

The oxidation of step (2) can be carried out with any of the known peroxidizing agents such as peracetic acid or hydrogen peroxide. For instance, 40% peracetic acid in an inert solvent such as acetic acid, chloroform, dichloroethane, trichlorothane, tetrachloroethane, chlorobenzene, dichlorobenzene, toluene or xylene, is quite effective. The peroxidation can also be carried out in a two-phase system with 30-60% aqueous hydrogen peroxide and an inert solvent such as the water-insoluble oils just named. Alternatively, 30-60% aqueous hydrogen peroxide can be used in a one-phase system with acetic acid as the solvent. The preferred agent and solvent for step (2) is 40% peracetic acid in xylene.

The acetyl-cleavage of step (3) is readily carried out with aqueous mineral acid, such as sulfuric acid, hydrobromic acid or hydrochloric acid. For an easy diazotization and replacement of the diazonium group in the next step, (4), hydrochloric acid is preferred. Furthermore, if it is desired to proceed directly to step (4), without isolation of compound III, hydrochloric acid would be further preferred in step (3), because it is also preferred in step (4).

The diazotization of step (4) is carried out under stronger acidic conditions than are commonly encountered in standard diazotization methods. The diazotization is effected with sodium nitrite and strong acids such as hydrochloric acid, hydrobromic acid, sulfuric acid or tetrafluoroboric acid, especially hydrochloric acid in strong concentration or a mixture of hydrochloric acid and tetrafluoroboric acid. When hydrobromic acid is used, bromine must be added, as taught by Lyman C. Craig, *Journal of Americal Chemical Society*, 56, 231 (1934). The resulting diazonium salt is then treated, in the second part of step (4), with hot hydrochloric or hydrobromic acid to give compound II where X is chlorine or bromine. Hydrochloric acid is preferred as is compound II where X is chlorine. The artisan will appreciate that other equivalents to sodium nitrite-hydrochloric acid may be used, such as nitrosylchloride in hydrochloric acid, or ammonium nitrite in hydrochloric acid.

In step (5), the replacement of the 2-chloro or 2-bromo group with a mercapto group can be effected by a sulfhydryl donor. By sulfhydryl donor is meant agents which generate actually, or in effect, sulfhydryl ions. Eligible sulfhydryl donors include alkali metal polysulfides, alkali metal sulfides, alkali metal hydrosulfides, thiourea, thioacetic acid, alkali metal trithiocarbonates, alkali metal thiosulfates and alkali metal thiophosphates. Among the alkali metals, sodium is preferred. Of the described sulfhydryl donors, sodium hydrosulfide and thiourea are preferred.

Methods of preparing heavy metal double salts of 2-mercaptopyridine-N-oxides are taught in the art, for instance, U.S. Pat. No. 2,809,971, which issued on Oct. 15, 1957, on the application of Jack Bernstein and Kathryn A. Loose.

EXAMPLE 1

2-Aminopyridine-1-Oxide Hydrochloride

To 70.5 g. of 2-aminopyridine, partially dissolved in 180 g. of xylene, was slowly added, with stirring, 79.6 g. acetic anhydride. The addition was carried out over a 20-minute period. The reaction vessel was water-cooled so as to maintain the reaction mixture at 30-40° C during the addition. The reaction solution was then heated for 1 hour at a temperature of 74°-78° C to give 2-acetamidopyridine, which was used without isolation.

The solution of 2-acetamidopyridine was chilled in an ice bath to 10°-15° C and treated with 118 g. of commercial 40% peracetic acid which was slowly added over a 40-minute period with ice-cooling and stirring. During the course of the addition the temperature was between 15°-25° C. After 1 hour stirring, with little cooling (temperature 20°-30° C), the turbid solution was heated for 3.5 hours at 70° C with stirring. To the clear hot solution were added 85 g. 37.5% hydrochloric acid and 37 g. water, and to the resulting cloudy solution was added 3.5 g. 37% formaldehyde solution to destroy any unreacted excess of peroxide compounds. The mixture was stirred and heated 2.5 hours at 80°-82° C. After cooling to room temperature, 40 g. xylene was added and the cloudy solution was evaporated, under vacuum, in a rotary evaporator, until the residue was solid. The resulting moist crystals were dried at 50°-60° C under vacuum, to give 116 g. of 2-aminopyridine-1-oxide hydrochloride, which on recrystallization from 1:1 ethanoltoluene mixture, weighed 98.8 g. The resulting colorless crystals gave a m.p. of 155°-156° C.

EXAMPLE 2

2-Aminopyridine-1-Oxide Hydrochloride

2-Aminopyridine (11.8 g.) was dissolved in 25 ml dichloroethane and the resulting clear solution chilled to 10°-15° C. Commercial 40% peracetic acid (20 g.) was slowly added over a 30-minute period with ice-cooling and stirring; the temperature was kept between 15°-20° C. After 1/2 hour stirring at 20°-30° C with very little cooling, the clear solution was allowed to react 15 hours at room temperature. Then was added 0.5 g. charcoal and the mixture kept at 70° C for 1 hour. The solution was filtered and the filtrate diluted with 100 ml dichloroethane. The clear solution was extracted twice with 30 ml of 20% hydrochloric acid. The acid extracts were washed with 30 ml dichloroethane and then evaporated under vacuum in a rotary evaporator to dryness to give 19.7 g. yellow crystals. Recrystallization from 1:1 ethanoltoluene mixture gave 13.7 g. nearly colorless crystals with m.p. 148°-152° C.

EXAMPLE 3

2-Chloropyridine-1-Oxide Hydrochloride

The moist crystals of 2-aminopyridine-1-oxide hydrochloride from Example 1, with or without drying and recrystallization, or the material of Example 2 after purification, can be used in this preparation without substantial difference in the results. A solution of 2-aminopyridine-1-oxide hydrochloride (110 g. dry weight) and 146 g. of concentrated hydrochloric acid (37.5%) in 158 g. of water was cooled to about 0° C and treated dropwise, with stirring, with 51.8 g. of sodium nitrite in 110 g. of water over a period of 1 hour with the temperature being maintained between −5° C and +5° C, to give a clear, orange solution of diazotized material. The orange solution was stirred for about 5 minutes at about 0° C, and was then immediately added by a cooled funnel, over a 40-minute period with stirring, to a hot solution of 110 g. 20% hydrochloric acid with the temperature of the reaction vessel being maintained at 95°-101° C. After 1/3 of the diazotized solution was added, 58.5 g. concentrated hydrochloric acid (37.5%) was poured into the hot reaction mixture. The addition of the remaining ⅔ of diazotized solution was then continued at the same rate and temperature, and stirring was then continued until nitrogen evolution ceased, about 7 minutes. This treatment yielded an aqueous solution of 2-chloropyridine-1-oxide hydrochloride, suitable for use as the solution in Examples 4 and 5. Isolation by vacuum evaporation, extraction from inorganic salts with absolute ethanol and recrystallization from ethanol-toluene gave purified material, m.p. 135°-137° C.

EXAMPLE 4

2-Mercaptopyridine-1-Oxide

The entire aqueous solution of 2-chloro-pyridine-1-oxide hydrochloride from Example 3 was treated with 30% aqueous sodium hydroxide to adjust the pH to 7.0 − 8.0 with stirring and cooling to maintain the temperature below about 40° C. In the neutralized solution 71 g.

sodium hydrogen sulfide dihydrate was dissolved. The reaction mixture that had a temperature of about 25° to 30° C was heated under nitrogen atmosphere up to 85° – 90° C. The ph was controlled with a glass electrode. At the beginning of heating, after the addition of the sodium hydrogen sulfide, the pH was about 11. As the temperature rose, the pH decreased. At a pH of 9.7, a 30% aqueous sodium hydroxide solution was added dropwise to adjust the pH between 9.7 and 10.7. When the pH was constant, and no more alkali solution was needed to maintain the 9.7 to 10.7 pH range, the clear solution was heated 20 minutes at 85° – 90° C. Then the solution was cooled to room temperature and neutralized with 20% hydrochloric acid under nitrogen atmosphere to a pH of 2.0 – 2.5. At this pH, 2-mercapto-pyridine-1-oxide separated from solution. The suspension was stirred at room temperature for about two hours before filtering. The filtration residue was washed four times with water and dried in vacuum at room temperature. Yield 79.5 g., m.p. 68°–69° C. Recrystallization from toluene-cyclohexane gave 72.5 g., m.p. 69°–70° C.

EXAMPLE 5

2-Mercaptopyridine-1-Oxide

The aqueous solution of 2-chloropyridine-1-oxide hydrochloride, produced in Example 3, was evaporated under vacuum, on a rotary evaporator at 50° C, to a syrup. The syrup was diluted by the addition of 380 g. of n-propanol, and the evaporation was then continued until 190 g. of n-propanol had been evaporated. Additional n-propanol (375 g.) was then added to give a cloudy solution. To the cloudy solution, under nitrogen atmosphere, at room temperature, 67.0 g. of thiourea was added with stirring. The reaction mixture was then stirred and heated at reflux for 20 minutes, becoming a thick slurry as the reaction proceeded. The mixture was then cooled to room temperature and filtered. The filter residue was washed with a little n-propanol and dissolved, under nitrogen, in 750 g. of water containing 90 g. of anhydrous sodium carbonate to give a clear brown solution. The brown solution was held under nitrogen for 5 hours at room temperature, and then acidified with 20% hydrochloric acid to pH of 2.0 to 2.5, at which point solid 2-mercaptopyrindine-1-oxide separated from solution. Isolation and purification as in Example 4 gave 50.0 g., m.p. 69°–71° C. In this Example, the final recrystallization is unnecessary.

EXAMPLE 6

Zinc Double Salt of 2-Mercaptopyridine-1-Oxide

Under a nitrogen atmosphere, 19.05 g. of material of Examples 4 or 5, without recrystallization, was dissolved in a solution of 6.1 g. sodium hydroxide in 100 ml water at a temperature of about 50° C. The resulting clear brown solution was cooled to room temperature. Over a period of 20 minutes, a solution of 21.55 g. zinc sulfate heptahydrate was added dropwise in 40 ml of water with stirring. The resulting viscous substance was strongly stirred for two hours and then filtered. The filtration residue was washed five times with water and once with ethanol and then dried in vacuum at about 80° C. Yield 22.1 g. white powder, m.p. 253°–255° C.

The zinc double salt of this Example can also be prepared from the brown solution (after 5 hours at room temperature and before acidification) of Example 5, without isolation of the 2-mercaptopyridine-1-oxide. The brown solution is filtered and treated dropwise with zinc sulfate as above in this Example, with similar results, but slightly lower melting point 240°–243° C. The isolated material of Example 5, treated with zinc sulfate as above gives the zinc double salt, comparable in yield and purity to that described in the first part of this Example.

EXAMPLE 7

Ring-Substituted 2-Mercaptopyridine-1-Oxides

By the methods of Examples 1 and 3–5, a series of ring-substituted 2-aminopyridines are converted to the corresponding ring-substituted 2-mercaptopyridine-1-oxides, via the 2-acetylamino derivatives of structure VI:

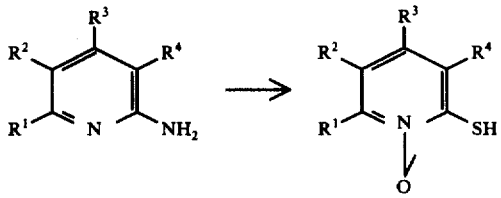

| Compound | R¹ | R² | R³ | R⁴ | m.p.(° C) |
|---|---|---|---|---|---|
| a | | Br | | | |
| b | | Cl | | | |
| c | | Cl | | Cl | |
| d | | NO₂ | | | |
| e | | | | CH₃ | 61 – 63° |
| f | CH₃ | | | | 52 – 54 |
| g | CH₃ | | CH₃ | | 106 – 108 |

Yields of 2-mercaptopyridines of structure I were in the range of 45% (compound g) to 75% (compound e), based on the corresponding 2-aminopyridine-1-oxide hydrochlorides of structure III. Conversion of the substituted 2-aminopyridines of structure IV to the intermediates of structure III was effected in about 80% yield.

In general, the ring-substituted 2-aminopyridine-1-oxides diazotize more readily than the unsubstituted example shown in Example 3, that is require less strongly acidic conditions. In each individual Example, the required acidity can be determined by test-tube experiment, by adding sodium nitrite to samples of different pH, adding phenol to couple under alkaline conditions, and selecting that original pH which gives a rapid and strong color change on coupling, indicative of diazotization. It should also be noted that most of the resulting ring-substituted diazonium salts are stabilized by the ring-substituents, so that excess acid strength is not of substantial concern.

As a variation of Example 1, the acetylation can be run without a solvent, as in Example 8. This is a useful variation when the peroxidation is to be carried out with hydrogen peroxide in acetic acid as in Example 8, but the procedure of Example 1 is preferred.

EXAMPLE 8

2-Amino-4-Methylpyridine-1-Oxide Hydrochloride

To 26.5 g. of acetic anhydride was added, in small portions, 27.1 g. of 2-amino-4-methylpyridine with cooling and stirring. The reaction temperature was kept below 60° C, and stirring was continued for 15 minutes without cooling after the addition was complete. The reaction solution was then heated at 75° – 80° C for 1.5 hours, with stirring. After the reaction solution was cooled to room temperature, 60 g. of acetic acid was added, followed by 40 g. of 30% hydrogen peroxide. The resulting reaction mixture was stirred at room temperature for 1 hour and then at about 75° C for 4 hours. While still hot the reaction solution was treated with 1 g. of activated charcoal. Heating and stirring was then continued for 1.5 hours. Hydrochloric acid (37%, 30 g. in 60 g. water) was added to the hot reaction mixture, and heating (80° C) and stirring were continued for 2 hours. The reaction mixture was cooled to room temperature and filtered. The filtrate was evaporated to dryness, under vacuum at 55° C. The resulting crystalline residue was recrystallized from 200 ml. of 1:1 ethanol-toluene to give 23.3 g. of colorless crystals, m.p. 198°–202° C.

I claim:

1. A process of manufacturing a 2-mercaptopyridine-1-oxide of the formula

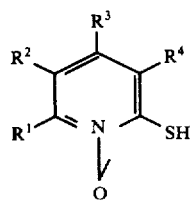

wherein $R^1$, $R^2$, $R^3$ and $R^4$ are hydrogen, fluorine, chlorine bromine, nitro, $C_1$ to $C_{12}$-alkyl, $C_1$ to $C_4$-alkoxy, benzyl, phenyl or phenoxy, provided at least two of $R^1$, $R^2$, $R^3$ and $R^4$ are hydrogen, comprising the steps of diazotizing the corresponding 2-aminopyridine-1-oxide and treating the resulting diazonium salt with hydrochloric acid or hydrobromic acid to give the corresponding 2-chloro- or 2-bromopyridine-1-oxide as the corresponding hydrohalide salt, followed by treatment with a sulfhydryl donor to give the 2-mercaptopyridine-1-oxide.

2. The process of claim 1, wherein the diazonium salt is treated with hydrochloric acid to give the corresponding 2-chloropyridine-1-oxide hydrochloride.

3. The process of claim 1, wherein $R^1$, $R^2$, $R^3$ and $R^4$ are hydrogen.

4. The process of claim 1, wherein the sulfhydryl-donor is sodium hydrogen sulfide or thiourea.

5. The process of claim 1, wherein the sulfhydryl-donor is sodium hydrogensulfide reacted at a pH in the range of 9.5 to 11.0.

* * * * *